(12) United States Patent
Sharma

(10) Patent No.: US 6,353,007 B1
(45) Date of Patent: Mar. 5, 2002

(54) SUBSTITUTED 1-(4-AMINOPHENYL) INDOLES AND THEIR USE AS ANTI-INFLAMMATORY AGENTS

(75) Inventor: Rajiv Sharma, Ridgefield, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/616,014

(22) Filed: Jul. 13, 2000

(51) Int. Cl.[7] .................. C07D 401/10; A61K 31/4439
(52) U.S. Cl. .................... 514/339; 514/333; 546/277.4; 546/256

(58) Field of Search .............................. 546/277.4, 256; 514/339, 333

(56) References Cited

PUBLICATIONS

CA 124:317209, Hemmi et al. 1996.*

* cited by examiner

*Primary Examiner*—Jane Fan
(74) *Attorney, Agent, or Firm*—R. P. Raymond; T. X. Witkowski; M-E. M. Devlin

(57) ABSTRACT

1-(4-Aminophenyl) indoles optionally substituted on the 2-,4-,5-,6- and 7-positions of the indole ring and on the amino group on the 4-position of the phenyl ring, which indoles inhibit IL-2 production in T-lymphocytes.

15 Claims, No Drawings

SUBSTITUTED 1-(4-AMINOPHENYL) INDOLES AND THEIR USE AS ANTI-INFLAMMATORY AGENTS

BACKGROUND OF THE INVENTION

It has been well established that T-cells play an important role in regulating immune response (F. Powrie and R. L. Coffman, Immunol. Today, 1993, 14, 270). Indeed, activation of T-cells is often the initiating event in many inflammatory and autoimmune diseases. IL-2 is an autocrine growth factor which plays an essential role in the regulation of T-cell activation and proliferation. Clinical studies have shown that interference with IL-2 activity effectively suppresses immune response in vivo (T. A. Waldmann, Immunol. Today, 1993, 14, 264). Accordingly, agents which inhibit IL-2 production are therapeutically useful for selectively suppressing immune response in a patient in need of such immunosuppression.

Previously, others have attempted to interfere with the activity of IL-2 by using cytokine antagonists, monoclonal antibodies, toxins and other biologics which seek to prevent IL-2 from binding to its receptor (G. Mazur and I. Frydecka, Acta Haematol. Pol., 1993, 24, 307, 1993). More recently, others have attempted to inhibit IL-2 production at the T-cell level, for example by blocking the expression of IL-2 MRNA with glucocorticoids or cyclosporin A. However, to date, the reported compounds suffer from several disadvantages such as low potency, poor in vivo activity, toxicity and poor oral bioavailability. Accordingly, a need exists for compounds that can effectively inhibit IL-2 production for preventing and treating immune disorders.

U.S. application Ser. No. 09/324,933 discloses substituted 1-(4-aminophenyl)pyrazoles as anti-inflammatory agents. WO9919303 describes substituted phenyl-, heteroaryl- and heterocyclyl-substituted pyrazoles as useful in the treatment of allergy, inflammatory and autoimmune diseases. WO9951580 describes substituted pyrazoles as inhibitors of cytokine production.

BRIEF SUMMARY OF THE INVENTION

The compounds of this invention are 1-(4-aminophenyl) indoles optionally substituted on the 2-, 4-, 5-, 6- and 7-positions of the indole ring and on the amino group on the 4-position of the phenyl ring, having antiinflammatory activity by virtue of their ability to inhibit IL-2 production in T-lymphocytes.

In its broadest generic aspect, the invention comprises 1-(4-aminophenyl)indoles of Formula I.

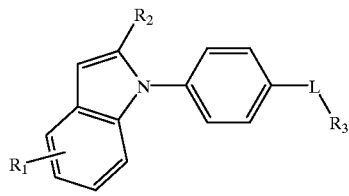

Formula I wherein:

$R_1$ is optionally in the 4-, 5-, 6-, or 7-position of the indole and, $R_1$ and $R_2$ which may be the same or different, are H; $CF_3$; halogen; CN; branched or unbranched $C_{1-8}$ alkyl; branched or unbranched $C_{2-8}$ alkenyl; $C_{3-8}$ cycloalkyl optionally substituted with OH, CN, or methoxy; $C_{1-8}$ alkoxy; $C_{1-4}$ alkyloxyalkyl; $C_{1-8}$ alkylthio; $C_{1-4}$ alkylthioalkyl; $C_{1-8}$ dialkylamino; $C_{1-4}$ dialkylaminoalkyl; $CO_2R_4$ where $R_4$ is $C_{1-4}$ alkyl or $C_{2-4}$ alkenyl optionally substituted with carbocyclyl or heterocyclyl; aryl or heterocyclyl connected to the indole in any position that makes a stable bond which aryl or heterocyclyl may be optionally substituted with halogen, $C_{1-4}$ alkyl, $C_{2-4}$ alkenyl, CN, $Me_2N$, $CO_2Me$, OMe, aryl, heterocyclyl, or $R_4$;

L is —NHC(O)—; —NHC(O)O—; —NHC(O)C(O)—; —NHC(S)—; —NH—; —NHC(O)NH—; —NHC(S)NH—; —NHCH$_2$—; —NHCH($R_5$)— where $R_5$ is H, CN, $C_{1-6}$ alkyl, $C_{1-6}$ alkyloxyalkyl $C_{1-6}$ alkythioalkyl, $C_{1-6}$ alkylsulfinylalkyl, $C_{1-6}$ alkysulfonylalkyl, $C_{3-6}$ cycloalkyl, heterocyclyl or aryl optionally substituted with a halogen, $C_{1-4}$ alkyl, CN, $Me_2N$, $CO_2Me$ or OMe; or L is —NHC($R_5$)-lower alkyl;

$R_3$ is $C_{1-8}$ alkyl; $C_{1-8}$ alkyloxy; $C_{1-8}$ alkylthio; $C_{1-8}$ alkylamino; $C_{1-4}$ alkoxyalkyl; $C_{1-4}$ alkylthioalkyl; $C_{1-4}$ alkylaminoalkyl; $C_{1-4}$ dialkylalkylaminoalkyl; carbocyclyl or heterocyclyl, which carbocyclyl or heterocyclyl may optionally be substituted with one or more of the following: halogen, —CN, —NO$_2$, —SO$_2$NH$_2$ or $R_6$ (where $R_6$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkyl -sulfinylalkyl, $C_{1-6}$ alkysulfonylalkyl or $C_{2-6}$ alkynyl) and $R_6$ may be optionally substituted with halogen, —OH, alkyloxy, —CN, —COO-lower alkyl, —CONH-lower alkyl, —CON (lower alkyl)$_2$, dialkylamino, phenyl or heterocyclyl; or $R_3$ is —CO$_2R_6$; —N($R_6$)2; —NH($R_6$); —C(O)$R_6$; —OR$_6$; S(O)$_n$R$_6$ where n is 0, 1 or 2; —SO$_2$NHR$_6$; or —SO$_2$N ($R_6$)$_2$; or a pharmaceutically acceptable derivative thereof.

DETAILED DESCRIPTION OF THE INVENTION

In order that the invention herein described may be more fully understood, the following detailed description is set forth. As used herein, the following abbreviations are used:

DMF is dimethylformamide;
DMSO is dimethylsulfoxide;
Et is ethyl;
EtOAc is ethyl acetate;
EtOH is ethanol
Me is methyl;
MeOH is methanol;
THF is tetrahydrofuran; and
EDC is 1-(3-dimethylaminopropyl)-3-ethylcarbodimide hydrochloride.

Also, as used herein, each of the following terms, used alone or in conjunction with other terms, are defined as follows (except where noted to the contrary):

The term "alkyl" refers to a saturated aliphatic radical containing from one to ten carbon atoms. "Alkyl" refers to both branched and unbranched alkyl groups. Preferred alkyl groups are straight chain alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms. "Alkyl", as used herein, includes unsubstituted alkyl radicals, those radicals that are partially or fully halogenated and those radicals substituted with one to four, preferably one or two, substituents selected from amino, cyano, nitro, methoxy, ethoxy and hydroxy. The term "cycloalkyl" refers to the cyclic analog of an alkyl group, as defined above. Preferred cycloalkyl groups are saturated cycloalkyl groups containing from three to eight carbon atoms, and more preferably three to six carbon atoms. "Alkyl" and "cycloalkyl", as used herein, include unsubstituted alkyl and cycloalkyl radicals, those radicals that are partially or fully halogenated and those radicals substituted with one to four, preferably one or two, substituents selected from halo, amino, cyano, nitro, methoxy, ethoxy and hydroxy. It should be understood that any combination term using an "alk" or "alkyl" prefix refers to analogs according to the above definition of "alkyl". For example, terms such as "alkoxy" or "alkythio" refer to alkyl groups linked to a second group via an oxygen or sulfur atom.

The terms "alkenyl" and "alkynyl" refer to a mono- or polyunsaturated aliphatic hydrocarbon radical containing from two to twelve carbon atoms, containing at least one double or triple bond, respectively. "Alkenyl" and "alkynyl" refer to both branched and unbranched alkenyl and alkynyl groups. Preferred alkenyl and alkynyl groups are straight chain alkenyl or alkynyl groups containing from two to eight carbon atoms and branched alkenyl or alkynyl groups containing from five to ten carbon atoms. More preferred alkenyl and alkynyl groups are straight chain alkenyl or alkynyl groups containing from two to six carbon atoms and branched alkenyl or alkynyl groups containing from five to eight carbon atoms. "Alkenyl" and "alkynyl", as used herein, include unsubstituted alkenyl or alkynyl radicals, those radicals that are partially or fully halogenated and those radicals substituted with one to four, preferably one or two, substituents selected from halo, amino, cyano, nitro, methoxy, ethoxy and hydroxy.

The term "aryl" refers to phenyl and naphthyl, phenyl and naphthyl that are partially or fully halogenated and phenyl and naphthyl substituted with halo, alkyl, hydroxy, nitro, —COOH, —CO(lower alkoxy), —CO(lower alkyl), amino, alkylamino, dialkylamino, alkoxy, —NCOH, —NCO(lower alkyl), —NSO$_2$-Ph(halo)$_{0-3}$, Ph, —O-Ph; naphthyl, —O-naphthyl, pyrrolyl, pyrrolyl substituted with lower alkyl, pyridyl, pyridinyl, pyrazinyl, pyrimidinyl and pyridazinyl.

The term "halo" refers to a halogen radical selected from fluoro, chloro, bromo or iodo. Preferred halo groups are fluoro, chloro and bromo.

The term "carbocyclyl" refers to a stable 3–8 membered (but preferably 5 or 6 membered) monocyclic or 7–11 membered bicyclic radical which may be either saturated or unsaturated, aromatic or non-aromatic. Preferred carbocycles include, for example, phenyl, naphthyl, cyclopropyl, cyclobutyl, cyclopentyl, cyclohexyl, cycloheptyl, cyclopentenyl, cyclohexenyl, cycloheptenyl, indanyl, indenyl, dihydronaphthyl and tetrahydronaphthyl. Most preferred heterocycles of this invention are phenyl, naphthyl, cyclohexyl, tetrahydronaphthyl and indanyl. "Carbocyclyl" refers to unsubstituted carbocyclic radicals, those radicals that are partially or fully halogenated and those radicals substituted with alkyl; hydroxyl; nitro; —COOH; —CO(lower alkoxy); —CO(lower alkyl); amino; alkylamino; dialkylamino; alkoxy; —NCOH; —NCO(lower alkyl); —NSO$_2$-Ph(halo)$_{0-3}$, Ph; —O-Ph; naphthyl; —O-naphthyl; pyrrolyl; pyrrolyl substituted with lower alkyl; pyridyl; pyridinyl; pyrazinyl; pyrimidinyl and pyridazinyl.

The term "heterocycle" refers to a stable 5–8 membered (but preferably 5 or 6 membered) monocyclic or 8–11 membered bicyclic heterocycle radical which may be either saturated or unsaturated, aromatic or non-aromatic, and which may be optionally benzo- or pyridofused if monocyclic. Each heterocycle consists of carbon atoms and from 1 to 4 heteroatoms selected from the group consisting of nitrogen, oxygen and sulfur. As used herein, "nitrogen" and "sulfur" include any oxidized form of nitrogen and sulfur and the quaternized form of any basic nitrogen. The heterocycle may be attached by any atom of the cycle, which results in the creation of a stable structure. Preferred heterocycles include, for example, benzimidazolyl, furyl, imidazolyl, imidazolinyl, imnidazolidinyl, quinolinyl, isoquinolinyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiomorpholinyl, furyl, thienyl, triazolyl, thiazolyl, β-carbolinyl, tetrazolyl, thiazolidinyl, benzofuranoyl, thiomorpholinyl sulfone, benzoxazolyl, oxopiperidinyl, oxopyrrolidinyl, oxoazepinyl, azepinyl, isoxazolyl, tetrahydropyranyl, tetrahydrofuranyl, thiadiazoyl, benzodioxolyl, tetrahydrothiophenyl and sulfolanyl. Most preferred heterocycles of this invention include imidazolyl, pyridyl, pyrrolyl, pyrazolyl, piperidinyl, morpholinyl, furyl, thienyl, thiazolyl and the benzo- and pyrido-fused derivatives thereof. "Heterocyclyl" refers to unsubstituted heterocycle radicals, those radicals that are partially or fully halogenated and those radicals substituted with alkyl, hydroxyl, nitro, —COOH, —CO(lower alkoxy), —CO(lower alkyl), amino, alkylamino, dialkylamino, alkoxy, —NCHO, —NCO(lower alkyl), —NSO$_2$-Ph(halo)$_{0-3}$, Ph, —O-Ph, naphthyl, —O-naphthyl, pyrrolyl, pyrrolyl substituted with lower alkyl, pyridyl, pyridinyl, pyrazinyl, pyrimidinyl and pyridazinyl.

The term "lower" used in conjunction with other terms (e.g., "alkyl", "alkoxy" and the like) refers to a radical containing from one to six, preferably from one to five and more preferably, from one to four carbon atoms. For example, a "lower alkyl" group is a branched or unbranched alkyl radical containing from one to six carbon atoms.

The term "patient" refers to a warm-blooded animal, and preferably a human.

The term "pharmaceutically acceptable carrier" or "pharmaceutically acceptable adjuvant" refers to a non-toxic carrier or adjuvant that may be administered to a patient together with a compound of this invention and which does not destroy the pharmacological activity of that compound.

It should be understood that any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic center may be in the R or S configuration, or a combination of configurations.

The compounds of this invention are defined to include pharmaceutically acceptable derivatives thereof. A "pharmaceutically acceptable derivative" refers to any pharmaceutically acceptable salt, ester, or salt of an ester of a compound of this invention, or any other compound which, upon administration to a patient, is capable of providing (directly or indirectly) a compound of this invention, a pharmacologically active metabolite or pharmacologically active residue thereof.

Combinations of substituents and variables encompassed by this invention are only those that result in the formation of stable compounds. The term "stable" as used herein, refers to compounds which possess stability sufficient to permit manufacture and administration to a patient by conventional methods known in the art. Typically, such compounds are stable at a temperature of 40° C. or less, in the absence of moisture or other chemically reactive conditions, for at least a week.

The compounds of this invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, tosylate and undecanoate.

This invention relates to substituted 1-(4-aminophenyl) indoles and analogs thereof that inhibit interleukin-2 (IL-2) production. In one embodiment, this invention relates to a novel class of substituted 1-(4-aminophenyl)indoles and pharmaceutical compositions comprising these compounds. Because of their selective immunomodulating properties, the compounds and pharmaceutical compositions of this invention are particularly well suited for preventing and treating immune disorders, including autoimmune disease, inflammatory disease, organ transplant rejection and other disorders associated with IL-2 mediated immune response.

The substituted 1-(4-aminophenyl)indoles of this invention are represented by Formula I.

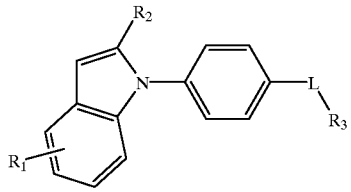

Formula I wherein:

R, is optionally in the 4-, 5-, 6-, or 7-position of the indole and, $R_1$ and $R_2$ which may be the same or different, are H; $CF_3$; halogen; CN; branched or unbranched $C_{1-8}$ alkyl; branched or unbranched $C_{2-8}$ alkenyl; $C_{3-8}$ cycloalkyl optionally substituted with OH, CN, or methoxy; $C_{1-8}$ alkoxy; $C_{1-4}$ alkyloxyalkyl; $C_{1-8}$ alkylthio, $C_{1-4}$ alkylthioalkyl; $C_{1-8}$ dialkylamino; $C_{1-4}$ dialkylaminoalkyl; $CO_2R_4$ where $R_4$ is $C_{1-4}$ alkyl or $C_{2-4}$ alkenyl optionally substituted with carbocyclyl or heterocyclyl; aryl or heterocyclyl connected to the indole in any position that makes a stable bond which aryl or heterocyclyl may be optionally substituted with halogen, $C_{1-4}$ alkyl, $C_{2-4}$ alkenyl, CN, $Me_2N$, $CO_2Me$, OMe, aryl, heterocyclyl, or $R_4$;

L is —NHC(O)—; —NHC(O)O—; —NHC(O)C(O)—; —NHC(S)—; —NH—; —NHC(O)NH—; —NHC(S) NH—; —NHCH$_2$—; —NHCH($R_5$)— where $R_5$ is H, CN, $C_{1-6}$ alkyl, $C_{1-6}$ alkyloxyalkyl $C_{1-6}$ alkythioalkyl, $C_{1-6}$ alkylsulfinylalkyl, $C_{1-6}$ alkysulfonylalkyl, $C_{3-6}$ cycloalkyl, heterocyclyl or aryl optionally substituted with a halogen, $C_{1-4}$ alkyl, CN, $Me_2N$, $CO_2Me$ or OMe; or L is —NHC($R_5$)-lower alkyl;

$R_3$ is $C_{1-8}$ alkyl; $C_{1-8}$ alkyloxy; $C_{1-8}$ alkylthio; $C_{1-8}$ alkylamino; $C_{1-4}$ alkoxyalkyl; $C_{1-4}$ alkylthioalkyl; $C_{1-4}$ alkylaminoalkyl; $C_{1-4}$ dialkylalkylaminoalkyl; carbocyclyl or heterocyclyl, which carbocyclyl or heterocyclyl may optionally be substituted with one or more of the following: halogen, —CN, —NO$_2$, —SO$_2$NH$_2$ or $R_6$ (where $R_6$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkyl-sulfinylalkyl, $C_{1-6}$ alkysulfonylalkyl or $C_{2-6}$ alkynyl) and $R_6$ may be optionally substituted with halogen, —OH, alkyloxy, —CN, —COO-lower alkyl, —CONH-lower alkyl, —CON(lower alkyl)$_2$, dialkylamino, phenyl or heterocyclyl; or $R_3$ is —CO$_2R_6$; —N($R_6$)$_2$; —NH($R_6$); —C(O)$R_6$; —OR$_6$; —S(O)$_nR_6$ where n is 0, 1 or 2; —SO$_2$NHR$_6$; or —SO$_2$N($R_6$)$_2$; or a pharmaceutically acceptable derivative thereof.

Preferably, the novel substituted 1-(4-aminophenyl) indoles of Formula I are those wherein:

$R_1$ is H, straight-chained, branched or cyclo- $C_{3-8}$ alkyl, alkenyl or alkynyl; $C_{1-3}$ alkyloxyalkyl; $C_{1-5}$ alkyloxy; $C_{1-3}$ alkylthioalkyl, $C_{1-5}$ alkylthio; $CF_3$; heterocyclyl or aryl optionally substituted with halogen, $C_{1-4}$ alkyl, —CN, alkoxy or $Me_2N$—;

$R_2$ is halogen, Me, Et, $CF_3$, —CN, cyclopropyl, vinyl, —SMe, —OMe, heterocyclyl or aryl optionally substituted with halogen, $C_{1-4}$ alkyl, —CN, alkoxy or $Me_2N$—;

L is —NHC(O)—, —NH—, —NHC(O)NH or —NHCH ($R_5$)—, where $R_5$ is H, $C_{1-4}$ alkyl, or —CN and $R_3$ is $C_{1-6}$ alkyl; $C_{1-4}$ alkyloxyalkyl; $C_{1-4}$ alkylthioalkyl; cyclohexyl, cyclopentyl, indanyl, indolyl, phenyl, thienyl, naphthyl, isoxazolyl or pyridyl optionally substituted with one or more halogen, —CN, —NO$_2$, —SO$_2$NH$_2$, or $R_6$ (where $R_6$ is $C_{1-6}$ alkyl, $C_{2-6}$ alkenyl, $C_{1-6}$ alkyloxyalkyl, $C_{1-6}$ alkylthioalkyl, or $C_{2-6}$ alkynyl) and $R_6$ may be optionally substituted with —OH, —CN, —COO-lower alkyl, —CONH-lower alkyl, —CON(lower alkyl)$_2$, dialkylamino, or heterocyclyl; —CO$_2R_6$, —N($R_6$)$_2$; —NH($R_6$); —C(O)$R_6$; —OR$_6$, —S(O)$_nR_6$ where n is 0, 1 or 2; —SO$_2$NHR$_6$; or —SO$_2$N($R_6$)$_2$.

More preferred are novel substituted 1-(4-aminophenyl) indoles of Formula I wherein:

$R_1$ is in the 4- or 5-position of the indole and, $R_1$ is H, i-Pr, $CF_3$, 3-pyridyl or 4-pyridyl;

$R_2$ is —CN, $CF_3$, Cl, Me, —SMe or Et;

L is —NHC(O)—, —NH— or —NHCH$_2$—; and $R_3$ is a phenyl ring which is optionally substituted with $O(CH_2)_3R_8$, where $R_8$ is —CN, —OH or 2-(1,3-dioxolanyl); —OC$_{3-4}$alkyl, —O(CH$_2$)$_4$OH, 1-pentenyl, one to three groups selected from Me, Cl, F and —CN; 3-pyridyl optionally substituted in the 6-position with —O(CH$_2$)$_2$OEt or —O(CH$_2$)$_3R_8$, where $R_8$ is —CN, —OH or 2-(1,3-dioxolanyl); 4-pyridinyl optionally substituted with a chlorine, 2-thienyl optionally substituted with Me or Br, 3,5-dimethyl-4-isoxazolyl, 1-methyl-2-indolyl, cyclopentyl, cyclohexyl, 1-indanyl or n-pent-3-yl.

Especially preferred are novel substituted 1-(4-aminophenyl)indoles of Formula I wherein:

$R_1$ is in the 4- or 5-position of the indole and, $R_1$ is H, i-Pr, $CF_3$, 3-pyridyl or 4-pyridyl;

$R_2$ is CN, $CF_3$, Cl, Me, SMe or Et;

L is —NHC(O)—, —NH— or —NHCH$_2$—; and $R_3$ is a phenyl ring which is optionally substituted with —O(CH$_2$)$_3$R$_8$, where $R_8$ is CN, OH or 2-(1,3-dioxolanyl); OC$_{3-4}$alkyl, O(CH$_2$)$_4$OH, 1-pentenyl, one to three groups selected from Me, Cl, F and CN; 3-pyridyl optionally substituted in the 6-position with O(CH$_2$)$_2$OEt or O(CH$_2$)$_3$R$_8$, where $R_8$ is CN, OH or 2-(1,3-dioxolanyl); 4-pyridinyl optionally substituted with a chlorine, 2-thienyl optionally substituted with Me or Br, 3,5-dimethyl-4-isoxazolyl, 1-methyl-2-indolyl, cyclopentyl, cyclohexyl, 1-indanyl or n-pent-3-yl.

Compounds of Formula I or Ia in which L is —NHC(O)— may be prepared by one of the methods outlined below. For example, a 1-(4-aminophenyl) substituted indole 1 may be reacted with a carboxylic acid 2 under suitable coupling conditions known to one skilled in the art, for example in the presence of EDC and a base catalyst such as N,N-dimethylaminopyridine in a suitable solvent such as methylene chloride, acetonitrile or DMF (Method A). Alternatively, 1 could be coupled with an acid halide 3 in the presence of a suitable base such as triethylamine in a suitable solvent such as methylene chloride (Method B).

Method A

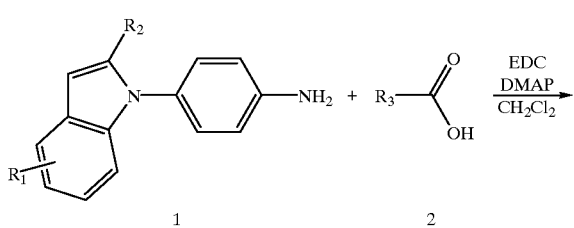

Method B

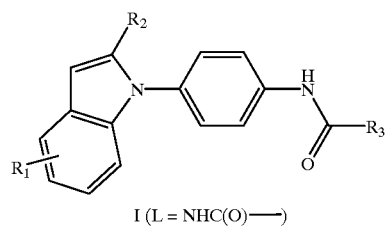

Compounds of Formula I or Ia in which L is —NH— and $R_3$ is a heteroaryl ring may be prepared, as illustrated below, by reaction of 1 with a heterocycle 4 containing a labile substituent such as a halogen, which may be displaced by nucleophilic substitution (Method C). The reaction may be carried out in a sealed tube or an open vessel, at ambient temperature or heated to 150° C. in a suitable solvent such as dioxane or THF. A base such as sodium bis-trimethylsilyl amide may be added to the reaction.

Method C

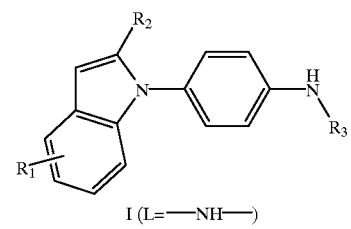

Compounds of Formula I in which L is —NHC(O)NH— may be prepared by reaction of isocyanate 5 with an amine 6 in a suitable solvent such as methylene chloride or toluene as illustrated for 1 in Method D. An amine such as triethylamine may be added. Alternatively, 1 could be reacted with an amine carbonyl chloride such as N-morpholine carbonyl chloride 7 in a suitable solvent such as methylene chloride (Method E). Intermediates 5 may be prepared from the corresponding 1 by methods known to those skilled in the art, for example by reaction of 1 with phosgene or a phosgene equivalent in the presence of a suitable base such as potassium carbonate, in a suitable solvent, such as methylene chloride.

Method D

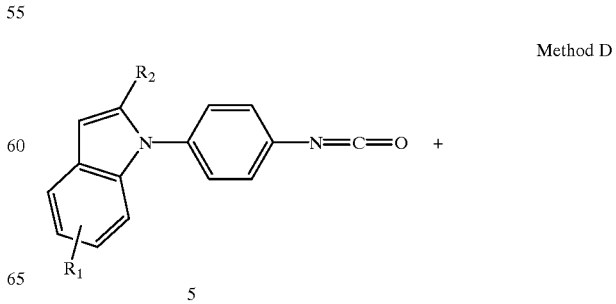

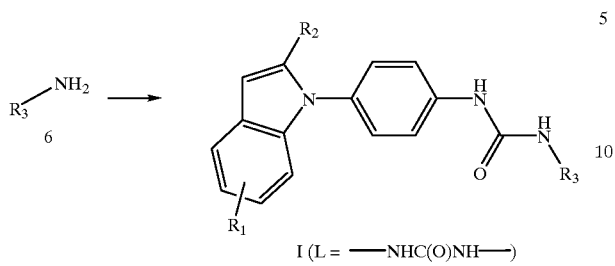

I (L = —NHC(O)NH—)

Method E

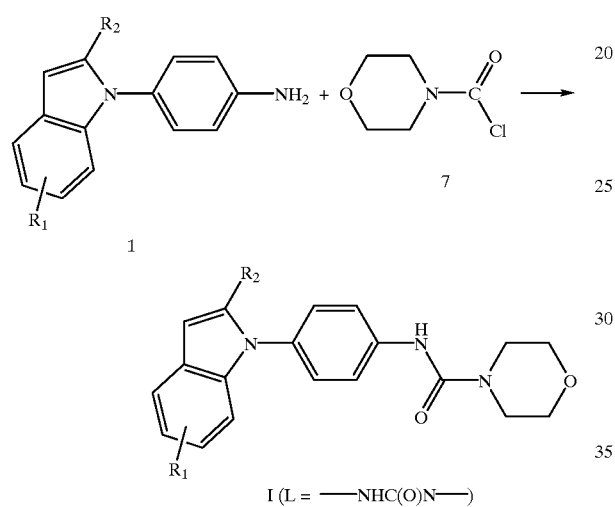

I (L = —NHC(O)N—)

Methods by which compounds of Formula I in which L is —NHCH(R$_5$)— or —NHCH$_2$— may be prepared are illustrated below. For example, these compounds may be prepared by reduction of the corresponding amide (L is —NHC(O)—) with a suitable reducing agent such as lithium aluminum hydride, in a suitable solvent such as THF or diethyl ether (Method F). Alternatively, amine 1 could react with an alkylating agent 8 (Method G) where X is a suitable leaving group such as a halogen. In another alternate procedure, amine 1 could react with an aldehyde 9, and the intermediate imine 10 reacted with a reducing agent such as sodium cyanoborohydride or sodium triacetoxyborohydride (Method H). Alternatively, 10 could be reacted with a nucleophile such as an alkyl or aryl lithium reagent (Method I).

Method F

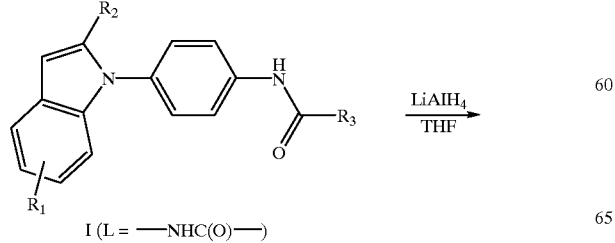

I (L = —NHC(O)—)

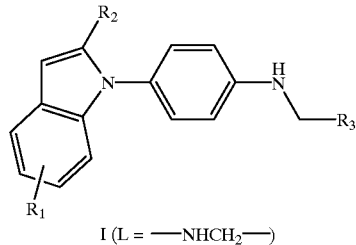

I (L = —NHCH$_2$—)

Method G

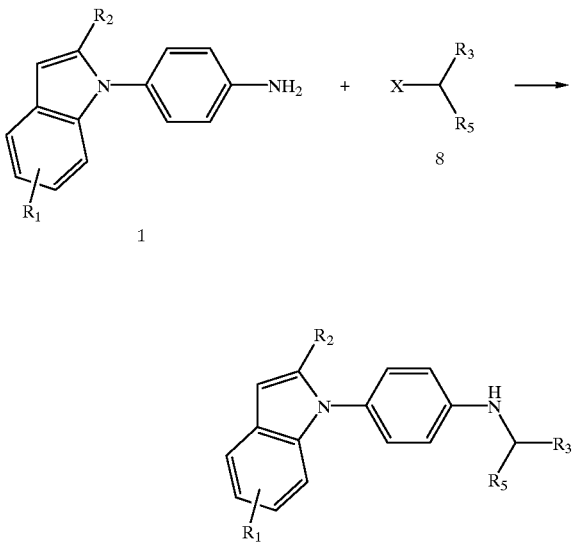

I (L = NHCH(R$_5$)—)

Method H and I

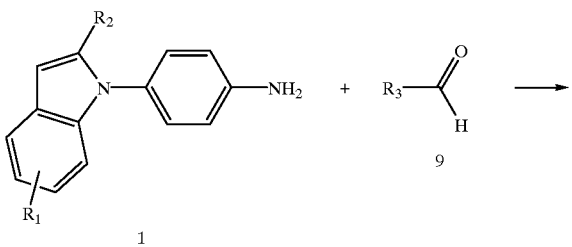

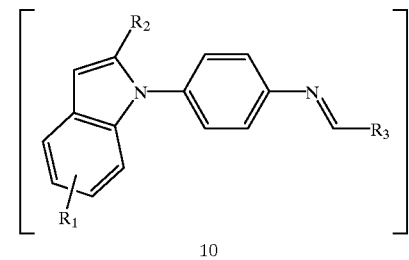

10

-continued

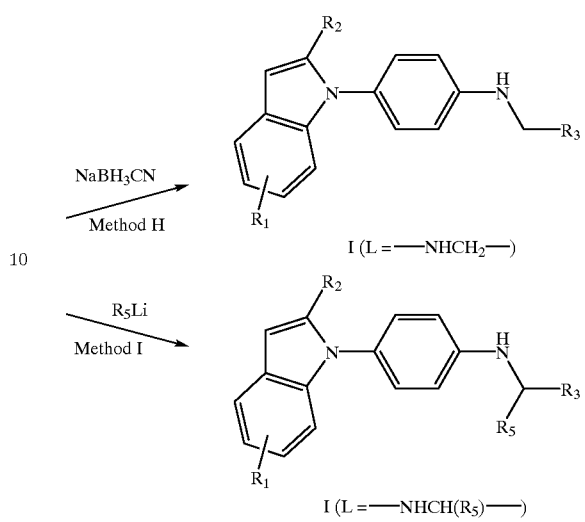

Method J describes an alternate procedure for preparing compounds of Formula I, where L is —NH—. Intermediate 1 may be heated at about 70° C. with an aryl bromide in the presence of a palladium catalyst, preferably Pd$_2$(dba)$_3$, 2,2'-bis(diphenylphosphino)-1,1'-binapthyl (BINAP), and a base, preferably NaOt-Bu, in a solvent such as toluene, as described by S. al.(J. Amer. Chem. Soc., 1993, 119, 8451). Alternately, one could employ the same conditions with the bromophenylindole 11 and an amine, R$_3$NH$_2$ Method J

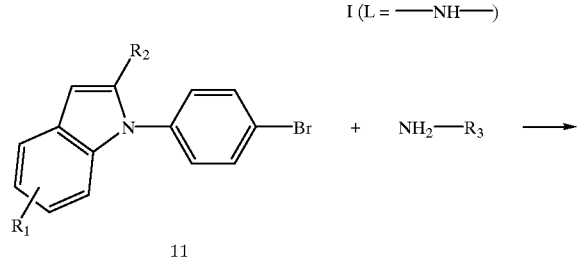

-continued

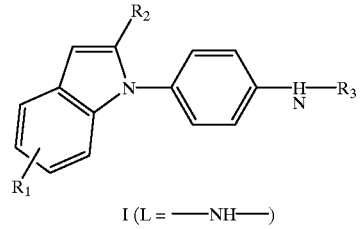

Preparation of intermediates used in the above procedures may be done by methods known to those skilled in the art and described in the chemical literature. For example, an optionally substituted indole 12 may be reacted with nitrobenzene substituted in the 4-position with a leaving group such as a halogen in the presence of a base (Method K). The nitrophenylindole produced (13) could then be reduced to an aminophenylindole (1) by using a reducing agent such as SnCl$_2$ or hydrogen or a hydrogen source such as ammonium formate in the presence of a catalyst such as palladium.

Method K

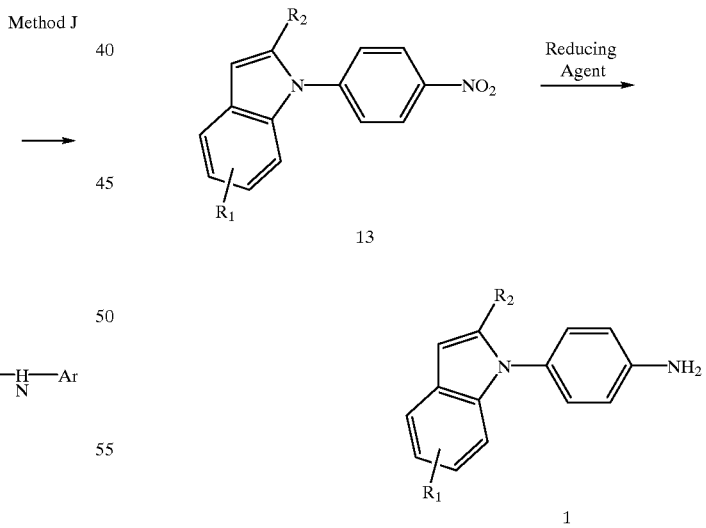

Indoles needed as intermediates in Method K are available commercially or readily prepared by methods known to those skilled in the art and reported in the chemical literature. For example, desired indole intermediates 12 may be prepared by the Fischer indole synthesis or one of its modifications (see for example, R. K. Brown, "Synthesis of the Indole Nucleus" in The Chemistry of Heterocyclic Compounds, V. 25, part 1, W. J. Houlihan, Ed., 1972; B.

Robinson, Chem. Reviews, 1969, 69; 227). As illustrated in Method L, an aryl hydrazine 14 is reacted with a ketone to form an aryl hydrazone 15. Treatment with an acid catalyst, such as hydrochloric acid, polyphosphoric acid, boron trifluoride or zinc chloride, provides the desired indole 12.

Method L

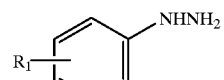
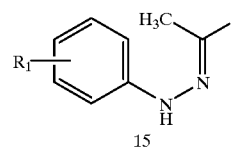

Other methods that may be used to prepare desired intermediates are reported in the chemical literature. For example, as described by J. Bergman et al. (J. Org. Chem., 1992, 57, 2495) and illustrated in Method M, a 2-chloroindole (12, $R_2$=Cl) may be prepared by reacting an indole with n-BuLi followed by $CO_2$ in a suitable solvent such as THF, at about −70° C., followed by reaction with t-BuLi and hexachloroethane and finally quenching with aqueous ammonium chloride. The 2-bromoindole analog may be prepared by substituting 1,2-dibromotetrachloroethane for the hexachloroethane.

As illustrated in Method N, the preparation of a 2-trifluoromethylindole (12, $R_2$ =$CF_3$) may be accomplished by irradiating an indole with UV light in the presence of difluoroiodomethane in DMF as described by Q.-Y. Chen and Z.-T. Li (J. Chem Soc. Perkin Trans. I, 1993, 645).

Method O illustrates the synthesis of 2-alkylthioindoles (12, $R_2$=Me or Et), prepared by treatment of a 3-alkylthioindole (16) with trifluoroacetic acid either neat, or in dichloromethane solution (R. Plate and C. J. Ottenheim, Tetrahedron, 1986, 42, 3349). The starting 3-alkylthioindols are readily prepared by methods known to those skilled in the art. For example, by reacting an indole dissolved in ether with methylmagnesium bromide, followed by zinc chloride and dimethylsulfide (C. C. Browder et al., Tetrahedron Lett., 1993, 34, 6245), one may prepare 3-methylthioindole (16, R'=Me). Alternatively, reaction of an alkylsulfenyl chloride with an indole in a suitable solvent such as methylene chloride or DMF provides a 3-alkylindole (T. J. Connolly and T. Durst, Tetrahedron Lett., 1997, 38, 1337; K. Anzai, J. Het. Chem., 1979, 16, 567).

Method M

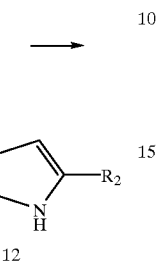

Method N

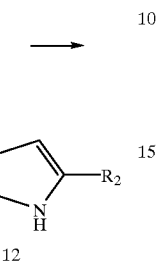

Method O

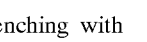
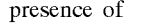
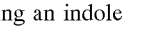

Several additional intermediates could be obtained from the 2-bromoindole 13 ($R_2$=Br) as illustrated below in Methods P-R. For example, as illustrated in Method P, 13 ($R_2$=Br) may be cross coupled with a terminal acetylene 17, where Z may be, for example, hydrogen or an alkyl group or any other group not adversely affecting the reaction, using conditions described by T. Sakamoto et al., (Synthesis, 1983, 312) to provide 13 with an alkyne at $R_2$. Alternatively, reaction with vinylstannanes 18, Z defined as above, under conditions described by J. W. Stille (Angew. Chem. Int. Ed. Engl., 1986, 25, 508), provides 13 with an alkene at $R_2$ ( Method Q). Reaction with substituted or unsubstituted aryl- or heteroarylboronic acids (19) under conditions described by N. Miyaura et al. (Chem. Rev. 1995, 95, 2457) provides 13 with aryl or heteroaryl groups at $R_2$ (Method R). Alkynes and alkenes may be converted to the corresponding alkyl groups by reduction with a suitable reducing agent such as hydrogen in the presence of a suitable catalyst such as platinum or palladium (see Method J) to provide desired 1, with an alkyl group at $R_2$. Alternatively, reaction with a reducing agent that leaves alkenes and alkynes intact, such as $SnCl_2$ provides 1 with alkenes or alkynes at $R_2$.

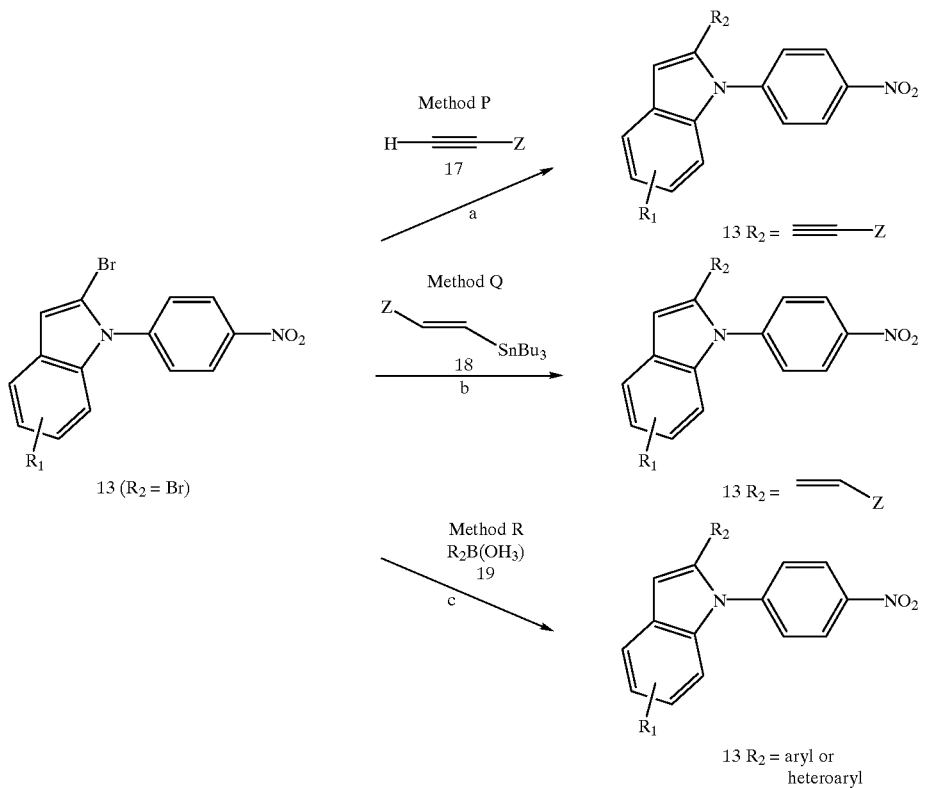

a. Pd(PPh₃)₄, CuBrSMe₂, Et₃N  b. Pd(PPh₃)₄, THF  c. Pd(PPh₃)₄, 2M Na₂CO₃, THF

As can be appreciated by chemists possessing ordinary skill in the art, the synthetic schemes described above are for illustrative purposes only and may be modified using conventional synthetic methodology to produce any of the analogs of Formula I. Depending on precisely how the synthetic schemes are modified, the specific reaction conditions might also require modification. Such modifications may involve the use of higher or lower temperature or pressure, conditions other than those reported herein, or the addition of further synthetic steps such as functional group transformations. However, since progress of the reactions is easily monitored by techniques such as high performance liquid chromatography, gas chromatography, mass spectroscopy, thin layer chromatography, nuclear magnetic resonance spectroscopy and the like, such modifications are well within the skill of the art. Likewise, it should be appreciated that initial products from these Methods could be further modified to make additional compounds of this invention. Intermediates used in the Methods described above may be commercially available or could be prepared from commercially available sources by methods described in the chemical literature and known to people skilled in the art.

The 1-phenylindole analogs of Formula I inhibit production of IL-2. Without wishing to be bound by theory, the compounds of this invention inhibit IL-2 production by T cells. This inhibition of IL-2 production is therapeutically useful for selectively suppressing immune function. The result of such selectively suppressed immunity includes reduced cell proliferation of peripheral blood lymphocytes and cellular immune response. Thus, the inhibition of IL-2 production is an attractive means for preventing and treating a variety of immune disorders, including inflammatory diseases, autoimmune diseases, organ and bone marrow transplant rejection and other disorders associated with IL-2 mediated immune response. In particular, the compounds of Formula I may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection) and lupus erythematosus. Other disorders associated with IL-2 mediated immune response will be evident to those of ordinary skill in the art and can also be treated with the compounds and compositions of this invention.

The compounds of this invention may be administered in any conventional dosage form in any conventional manner. Such methods of treatment, including their dosage levels and other requirements, may be selected by those of ordinary skill in the art from available methods and techniques. For example, a compound of this invention may be combined with a pharmaceutically acceptable carrier or adjuvant for administration to a patient in need of such treatment in a pharmaceutically acceptable manner and in an amount effective to treat (including lessening the severity of symptoms) the immune disorder.

The compounds of this invention may be administered alone or in combination with conventional therapeutics, such as conventional immunosuppressants. Advantageously, such combination therapies utilize lower dosages of the conventional therapeutics, thus avoiding possible toxicity and adverse side effects incurred when those agents are used as monotherapies. The compounds of this invention may be physically combined with the conventional therapeutics into a single pharmaceutical composition. Advantageously, the compounds may then be administered together in a single dosage form. Alternatively, the compounds may be administered separately (either serially or in parallel). Separate dosing allows for greater flexibility in the dosing regime.

According to this invention, the compounds of Formula I and the pharmaceutical compositions containing those compounds may be administered to a patient in any conventional manner and in any pharmaceutically acceptable dosage from, including, but not limited to, intravenously, intramuscularly, subcutaneously, intrasynovially, by infusion, sublingually, transdermally, orally, topically or by inhalation. The preferred modes of administration are oral and intravenous.

Dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger (1990)). Dosage levels and requirements are well-recognized in the art and may be selected by those of ordinary skill in the art from available methods and techniques suitable for a particular patient. Typically, dosage levels range from about 10–1000 mg/dose for a 70 kg patient. Although one dose per day may be sufficient, up to 5 doses per day may be given. For oral doses, up to 5000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto and the judgment of the treating physician.

Synthetic Example

In order that this invention be more fully understood, the following example is set forth. This example is for the purpose of illustrating preferred embodiments of this invention, and is not to be construed as limiting the scope of the invention in any way.

EXAMPLE 1

Synthesis of N-[4-(2-methylindol-1-yl)phenyl] pyridine-3-carboxamide

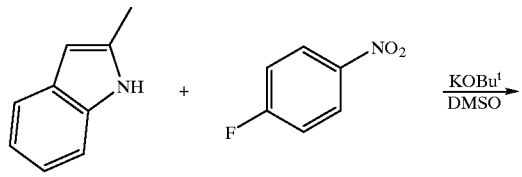

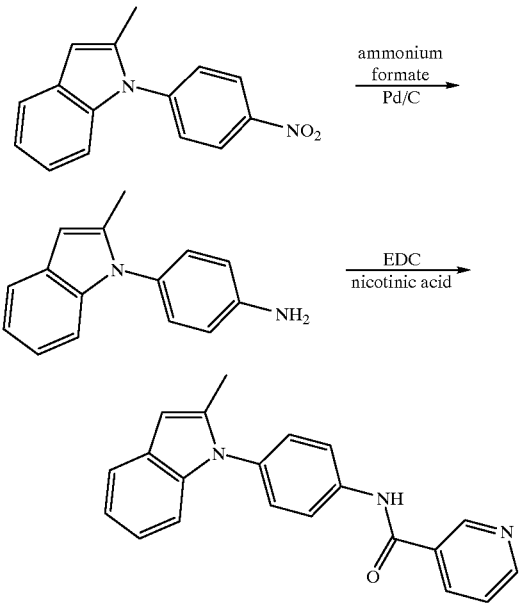

A solution of 2-methylindol (1 g, 7.6 mmol) and potassium t-butoxide (897 mg, 8 mmol) in DMSO (10 mL) was stirred at room temperature under argon for 30 min. 4-Fluoronitrobenzene (0.81 mL, 7.62 mmol) was added and the reaction mixture was heated to 100° C. in an oil bath for 5 h. The reaction mixture was diluted with water, extracted with EtOAc, the organic extract with washed with water and dried (MgSO$_4$). The oil obtained on concentration was flash chromatographed on silica gel and elution was -carried out with a gradient of 5–8% EtOAc in hexane to give 1-(4-nitrophenyl)-2-methylindol (500 mg).

To a stirred suspension of the above nitro compound (300 mg, 1.2 mmol) in EtOH (25 mL) and EtOAc (5 mL) was added solid ammonium formate (750 mg, 11.9 mmol) followed by 10% Pd—C (50 mg). The mixture was stirred for 2 h at room temperature, and then filtered through a short pad of diatomaceous earth and washed with EtOH/EtOAc. The filtrate was concentrated to give 1-(4-aminophenyl)-2-methylindol (0.22 g).

A mixture of the above amine (0.08 g, 0.36 mmol), nicotinic acid (114 mg, 0.59 mmol) and EDC (66 mg, 0.54 mmol) was dissolved in 2 mL acetonitrile and the reaction mixture was stirred overnight at room temperature. The reaction mixture was diluted with water, extracted with EtOAc, washed with water and dried (MgSO$_4$). The residue obtained on concentration was flash chromatographed on silica gel, eluting with a gradient of 2% MeOH in dichloromethane to give the title compound (40 mg).

The following examples may also be made by methods similar to those described above. Variations of the general methods and example above to obtained the desired compound can be achieved by one of ordinary skill in the art without undue experimentation:

N-[4-(2-Methylthioindol-1-yl)phenyl]pyridine-3-carboxamide;

(3-Methylthien-2-ylmethyl)-[4-(2-methylthioindol-1-yl) phenyl]amine;

N-[4-(2-Ethylindol-1-yl)phenyl]pyridine-3-carboxamide;

(2-Chloro-6-fluorobenzyl)-[4-(2-ethylindol-1-yl)phenyl] amine;

(2-Methylbenzyl)-[4-(2-ethylindol-1-yl)phenyl]amine;
[6-(3-Cyanopropoxy)pyridin-3-ylmethyl]-[4-(2-cyanoindol-1-yl)phenyl]amine;
[6-(3-[1,3]Dioxolan-2-ylpropoxy)pyridin-3-ylmethyl]-[4-(2-cyanoindol-1-yl)phenyl]amine;
N-[4-(2-Ethylindol-1-yl)phenyl]-1-methylindol-2-carboxamide;
(2-Chloro-6-fluorobenzyl)-[4-(2-cyanoindol-1-yl)phenyl]amine;
[(4-(2-Cyanoindol-1-yl)phenyl]-(2,6-dimethylbenzyl)-amine;
(2-Chloro-6-methylbenzyl)-[4-(2-cyanoindol-1-yl)phenyl]amine;
[4-(2-Cyanoindol-1-yl)phenyl]-(2-indanylmethyl)amine;
[4-(2-Ethylindol-1-yl)phenyl]-(2-indanylmethyl)amine;
[4-(2-Ethylindol-1-yl)phenyl]-(2-fluoro-6-methylbenzyl)amine;
4-(3-Cyanopropoxy)-N-[4-(2-cyanoindol-1-yl)phenyl]benzamide;
N-[4-(2-Cyanoindol-1-yl)phenyl]-4-(3-[1,3]dioxolan-2-yl-propoxy)benzamide;
[4-(3-Cyanopropoxy)benzyl]-[4-(2-ethylindol1-yl)phenyl]amine;
[4-(3-Cyanopropoxy)benzyl]-[4-(2-cyanoindol-1-yl)phenyl]amine.
N-[4-(2,4-Dimethylindol-1-yl)phenyl]pyridine-3-carboxamide;
N-[4-(4-Methyl-2-methylthioindol-1-yl)phenyl]pyridine-3-carboxamide;
N-[4-(2-Cyano-4-methylthioindol-1-yl)phenyl]pyridine-3-carboxamide;
N-[4-(5-Cyano-2-methylindol-1-yl)phenyl]pyridine-3-carboxamide;
N-[4-(2-Methyl-5-trifluoromethylindol-1-yl)phenyl]pyridine-3-carboxamide;
N-[4-(4-Methoxy-2-methylindol-1-yl)phenyl]pyridine-3-catboxamide;
N- {4-[2-Methyl-4-(3-pyridinyl)indol-1-yl)phenyl]pyridine-3-carboxamide;
N- {4-[2-Methyl-5-(3-pyridinyl)indol-1-yl)phenyl]pyridine-3-carboxamide;
N- {4-[2-Methyl-4-(4-pyridinyl)indol-1-yl)phenyl]pyridine-3-carboxamide;
N- {4-[2-Methyl-5-(4-pyridinyl)indol-1-yl)phenyl]pyridine-3-carboxamide;
N- {4-[2-Cyano-4-(3-pyridinyl)indol-1-yl)phenyl]pyridine-3-carboxamide;
N- {4-[2-Cyano-5-(3-pyridinyl)indol-1-yl)phenyl]pyridine-3-carboxamide;
N- {4-[2-Cyano-4-(4-pyridinyl)indol-1-yl)phenyl]pyridine-3-carboxamide;
N- {4-[2-Cyano-5-(4-pyridinyl)indol-1-yl)phenyl]pyridine-3-carboxamide;
N- {4-[2-Methylthio-4-(3-pyridinyl)indol-1-yl)phenyl]pyridine-3-carboxamide;
N- {4-[2-Methylthio-5-(3-pyridinyl)indol-1-yl)phenyl]pyridine-3-carboxamide;
N- {4-[2-Methylthio-4-(4-pyridinyl)indol-1-yl)phenyl]pyridine-3-carboxamide;
N- {4-[2-Methylthio-5-(4-pyridinyl)indol-1-yl)phenyl]pyridine-3-carboxamide;
N- {4-[2-Methyl-4-(2-tetrahydrofuranyl)indol-1-yl)phenyl]pyridine-3-carboxamide;
N- {4-[2-Methyl-5-(2-tetrahydrofuranyl)indol-1-yl)phenyl]pyridine-3-carboxamide;
N- {4-[2-Methyl-4-(3-tetrahydrofuranyl)indol-1-yl)phenyl]pyridine-3-carboxamide;
N- {4-[2-Methyl-5-(3-tetrahydrofuranyl)indol-1-yl)phenyl]pyridine-3-carboxamide;
N- {4-[2-Methyl-5-(3-tetrahydrofuranyl)indol-1-yl)phenyl]pyridine-3-carboxamide;
N- {4-[2-Cyano-4-(2-tetrahydrofuranyl)indol-1-yl)phenyl]pyridine-3-carboxamide;
N- {4-[2-Cyano-5-(2-tetrahydrofuranyl)indol-1-yl)phenyl]pyridine-3-carboxamide;
N- {4-[2-Cyano-4-(3-tetrahydrofuranyl)indol-1-yl)phenyl]pyridine-3-carboxamide;
N- {4-[2-Cyano-5-(3-tetrahydrofuranyl)indol-1-yl)phenyl]pyridine-3-carboxamide;
N- {4-[2-Methylthio-4-(2-tetrahydrofuranyl)indol-1-yl)phenyl]pyridine-3-carboxamide;
N- {4-[2-Methylthio-5-(2-tetrahydrofuranyl)indol-1-yl)phenyl]pyridine-3-carboxamide;
N- {4-[2-Methylthio-4-(3-tetrahydrofuranyl)indol-1-yl)phenyl]pyridine-3-carboxamide;
N- {4-[2-Methylthio-5-(3-tetrahydrofuranyl)indol-1-yl)phenyl]pyridine-3-carboxamide;
N- {4-[2-Methyl-4-(2-furanyl)indol-1-yl)phenyl]pyridine-3-carboxamide;
N- {4-[2-Methyl-5-(2-furanyl)indol-1-yl)phenyl]pyridine-3-carboxamide;
N- {4-[2-Methyl-4-(3-furanyl)indol-1-yl)phenyl]pyridine-3-carboxamide;
N- {4-[2-Methyl-5-(3-furanyl)indol-1-yl)phenyl]pyridine-3-carboxamide;
N- {4-[2-Cyano-4-(2-furanyl)indol-1-yl)phenyl]pyridine-3-carboxamide;
N- {4-[2-Cyano-5-(2-furanyl)indol-1-yl)phenyl]pyridine-3-carboxamide;
N- {4-[2-Cyano-4-(3-furanyl)indol-1-yl)phenyl]pyridine-3-carboxamide;
N- {4-[2-Cyano-5-(3-furanyl)indol-1-yl)phenyl]pyridine-3-carboxamide;
N- {4-[2-Methylthio-4-(2-furanyl)indol-1-yl)phenyl]pyridine-3-carboxamide;
N- {4-[2-Methylthio-5-(2-furanyl)indol-1-yl)phenyl]pyridine-3-carboxamide;
N- {4-[2-Methylthio-4-(3-furanyl)indol-1-yl)phenyl]pyridine-3-carboxamide;
N- {4-[2-Methylthio-5-(3-furanyl)indol-1-yl)phenyl]pyridine-3-carboxamide;
N- {4-[2-Methyl-4-(2-thiazolyl)indol -yl)phenyl]pyridine-3-carboxamide;
N- {4-[2-Methyl-5-(2-thiazolyl)indol-1-yl)phenyl]pyridine-3-carboxamide;
N- {4-[2-Cyano-4-(2-thiazolyl)indol-1-yl)phenyl]pyridine-3-carboxamide;
N- {4-[2-Cyano-5-(2-thiazolyl)indol-1-yl)phenyl]pyridine-3-carboxamide;
N- {4-[2-Methylthio-4-(2-thiazolyl)indol-1-yl)phenyl]pyridine-3-carboxamide and
N- {4-[2-Methylthio-5-(2-thiazolyl)indol-1-yl)phenyl]pyridine-3-carboxamide.

Assessment of Biological Properties

IL-2 Promoter Assay

The IL-2 promoter assay measures transcriptional activation of a luciferase reporter gene which has been placed under control of the IL-2 promoter/enhancer. All the known regulatory features of the IL-2 gene are contained within a ~300 bp sequence immediately upstream of the open reading frame. The region −328 to +35 relative to the transcription start site of the IL-2 gene is obtained by RT-PCR of human genomic DNA and is subcloned into the promoterless luciferase reporter vector pGL2-Basic (Promega). The resulting construct, pIL2P-luc, and a vector containing a neomycin resistance gene, pcDNA/Neo (Invitrogen), are linearized and stably transfected into Jurkat cells (a human T cell line) by electroporation. Following G-418 selection and dilution cloning, a cell line was established, J.1F/C6., which exhibited a strong induction of luciferase activity upon treatment with ionomycin and PMA (up to 100-fold), and potent inhibition by FK506 ($IC_{50}$=0.3 nM).

For screening compounds, the cells are pelleted by centrifugation, washed once with PBS, resuspended in RPMI (phenol red-free) containing 5% FBS, and dispensed into 96-well, white microtiter plates (Packard) at 50,000 cells/well. The cells are pre-incubated with compounds (1 μg/ml) for 15 min prior to addition of ionomycin (1 μg/ml) and PMA (10 ng/ml) in a final volume of 100 μl. Following a 5 hr incubation at 37° C. in a humidified incubator, 100 μl of Luc-Lite lysis buffer/luciferase assay buffer (Promega) is added and luminescence measured using a Packard Top-Count scintillation counter/luminometer.

The compounds described in the Synthetic Example was screened in this assay and had an $IC_{50}$ value below 10 microM While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments that have been presented herein by way of example.

What is claimed is:

1. A compound of Formula I

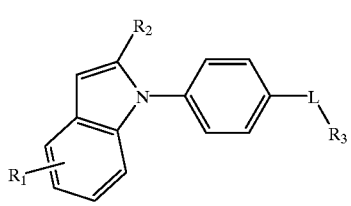

Formula I wherein:
$R_1$ is in the 4-, 5-, 6-, or 7-position of the indole, and
$R_1$ is H; $CF_3$; halogen; CN; branched or unbranched $C_{1-8}$ alkyl; branched or unbranched $C_{2-8}$ alkenyl; $C_{3-8}$ cycloalkyl optionally substituted with OH, CN, or methoxy; $C_{1-8}$ alkoxy; $C_{1-4}$ alkyloxyalkyl; $C_{1-8}$ alkylthio; $C_{1-4}$ alkylthioalkyl; $C_{1-8}$ dialkylamino; $C_{1-4}$ dialkylaminoalkyl; $CO_2R_4$; or aryl or heterocyclyl connected to the indole in any position that makes a stable bond and wherein the aryl thereof is optionally substituted with halogen, $C_{1-4}$ alkyl, $C_{2-4}$ alkenyl, CN, $Me_2N$, $CO_2Me$, OMe, aryl, heterocyclyl, or $R_4$;
$R_2$ is H; $CF_3$; halogen; CN; branched or unbranched $C_{1-8}$ alkyl; branched or unbranched $C_{2-8}$ alkenyl; $C_{3-8}$ cycloalkyl optionally substituted with OH, CN, or methoxy; $C_{1-8}$ alkoxy; $C_{1-4}$ alkyloxyalkyl; $C_{1-8}$ alkylthio; $C_{1-4}$ alkylthioalkyl; $C_{1-8}$ dialkylamino; $C_{1-4}$ dialkylaminoalkyl; $CO_2R_4$; or aryl connected to the indole in any position that makes a stable bond and wherein the aryl thereof is optionally substituted with halogen, $C_{1-4}$ alkyl, $C_{2-4}$ alkenyl, CN, $Me_2N$, $CO_2Me$, OMe, or aryl;

L is —NHC(O)—, —NHC(O)O—, —NHC(O)C(O)—, —NHC(S)—, —NHC(O)NH—, or —NHC(S)NH—;

$R_3$ is pyridyl optionally substituted with one or more of the following: halogen, CN, $NO_2$, $SO_2NH_2$, or $R_6$, wherein $R_6$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkyl-sulfinylalkyl, $C_{1-6}$ alkylsulfonylalkyl, or $C_{2-6}$ alkynyl, and $R_6$ is optionally substituted with halogen, OH, alkyloxy, CN, —COO-lower alkyl, —CONH-lower alkyl, —CON(lower alkyl)$_2$, dialkylamino, phenyl, or heterocyclyl; and $R_4$ is $C_{1-4}$ alkyl or $C_{2-4}$ alkenyl optionally substituted with carbocyclyl, or a pharmaceutically acceptable derivative thereof.

2. The compound according to claim 1, wherein:

$R_1$ is H; straight-chained, branched, or cyclo $C_{3-8}$ alkyl, alkenyl, or alkynyl; $C_{1-3}$ alkyloxyalkyl;

$C_{1-5}$ alkyloxy; $C_{1-3}$ alkylthioalkyl, $C_{1-5}$ alkylthio; $CF_3$; heterocyclyl or aryl optionally substituted with halogen, $C_{1-4}$ alkyl, CN, alkoxy or $Me_2N$; and $R_2$ is halogen, Me, Et, $CF_3$, CN, cyclopropyl, vinyl, SMe, OMe, or aryl optionally substituted with halogen, $C_{1-4}$ alkyl, CN, alkoxy, or $Me_2N$.

3. A compound of Formula I

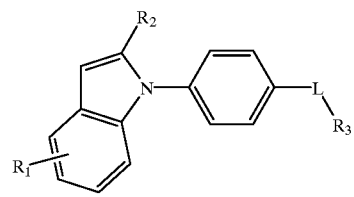

Formula I $R_1$ is in the 4- or 5-position of the indole, and $R_1$ is H, Et, i-Pr, n-Pr, t-Bu, cyclopentyl, $CF_3$, —OEt, $MeOCH_2$-, 2- or 3-tetrahydrofuranyl, 2-, 3-, or 4-pyridyl, 2-furanyl, or 2-thiazolyl;

$R_2$ is CN, $CF_3$, Cl, Me, Et, SMe, cyclopropyl, or vinyl;

L is —NHC(O)—, —NHC(O)O—, —NHC(O)C(O)—, or —NHC(O)NH—; and $R_3$ is 3-pyridyl or 4-pyridyl optionally substituted with one to three groups selected from Cl, Br, Me, CN, $CF_3$, $OCF_3$, $NO_2$, or $O(CH_2)_pR_7$, where p is 3 or 4 and $R_7$ is CN, $CO_2Me$ 2-(1,3-dioxolanyl), OH, or $OC_6H_5$, or a pharmaceutically acceptable derivative thereof.

4. A compound of Formula I

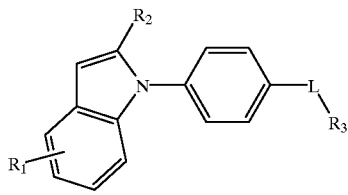

Formula I $R_1$ is in the 4- or 5-position of the indole, and
$R_1$ is H, i-Pr, $CF_3$, 3-pyridyl, or 4-pyridyl;
$R_2$ is CN, $CF_3$, Cl, Me, SMe, or Et;
L is —NHC(O)—, —NHC(O)O—, —NHC(O)C(O)—, or —NHC(O)NH—; and
$R_3$ is 3-pyridyl optionally substituted in the 6-position with $O(CH_2)_2OEt$ or $O(CH_2)_3R_8$, wherein $R_8$ is CN, OH, or 2-(1,3-dioxolanyl) or 4-pyridinyl optionally substituted with a chlorine,
or a pharmaceutically acceptable derivative thereof.

5. A compound selected from the group consisting of:
N-[4-(2-Methylindol-1-yl)phenyl]pyridine-3-carboxamide;
N-[4-(2-Methylthioindol-1-yl)phenyl]pyridine-3-carboxamide;
N-[4-(2-Ethylindol-1-yl)phenyl]pyridine-3-carboxamide;
N-[4-(2,4-Dimethylindol-1-yl)phenyl]pyridine-3-carboxamide;
N-[4-(4-Methyl-2-methylthioindol-1-yl)phenyl]pyridine-3-carboxamide;
N-[4-(2-Cyano-4-methylthioindol-1-yl)phenyl]pyridine-3-carboxamide;
N-[4-(5-Cyano-2-methylindol-1-yl)phenyl]pyridine-3-carboxamide;
N-[4-(2-Methyl-5-trifluoromethylindol-1-yl)phenyl]pyridine-3-carboxamide;
N-[4-(4-Methoxy-2-methylindol-1-yl)phenyl]pyridine-3-carboxamide;
N- {4-[2-Methyl-4-(3-pyridinyl)indol-1-yl)phenyl]pyridine-3-carboxamide;
N- {4-[2-Methyl-5-(3-pyridinyl)indol-1-yl)phenyl]pyridine-3-carboxamide;
N- {4-[2-Methyl-4-(4-pyridinyl)indol-1-yl)phenyl]pyridine-3-carboxamide;
N- {4-[2-Methyl-5-(4-pyridinyl)indol-1-yl)phenyl]pyridine-3-carboxamide;
N- {4-[2-Cyano-4-(3-pyridinyl)indol-1-yl)phenyl]pyridine-3-carboxamide;
N- {4-[2-Cyano-5-(3-pyridinyl)indol-1-yl)phenyl]pyridine-3-carboxamide;
N- {4-[2-Cyano-4-(4-pyridinyl)indol-1-yl)phenyl]pyridine-3-carboxamide;
N- {4-[2-Cyano-5-(4-pyridinyl)indol-1-yl)phenyl]pyridine-3-carboxamide;
N- {4-[2-Methylthio-4-(3-pyridinyl)indol-1-yl)phenyl]pyridine-3-carboxamide;
N- {4-[2-Methylthio-5-(3-pyridinyl)indol-1-yl)phenyl]pyridine-3-carboxamide;
N- {4-[2-Methylthio-4-(4-pyridinyl)indol-1-yl)phenyl]pyridine-3-carboxamide;
N- {4-[2-Methylthio-5-(4-pyridinyl)indol-1-yl)phenyl]pyridine-3-carboxamide;
N- {4-[2-Methyl-4-(2-tetrahydrofuranyl)indol-1-yl)phenyl]pyridine-3-carboxamide;
N- {4-[2-Methyl-5-(2-tetrahydrofuranyl)indol-1-yl)phenyl]pyridine-3-carboxamide;
N- {4-[2-Methyl-4-(3-tetrahydrofuranyl)indol-1-yl)phenyl]pyridine-3-carboxamide;
N- {4-[2-Methyl-5-(3-tetrahydrofuranyl)indol-1-yl)phenyl]pyridine-3-carboxamide;
N- {4-[2-Cyano-4-(2-tetrahydrofuranyl)indol-1-yl)phenyl]pyridine-3-carboxamide;
N- {4-[2-Cyano-5-(2-tetrahydrofuranyl)indol-1-yl)phenyl]pyridine-3-carboxamide;
N- {4-[2-Cyano-4-(3-tetrahydrofuranyl)indol-1-yl)phenyl]pyridine-3-carboxamide;
N- {4-[2-Cyano-5-(3-tetrahydrofuranyl)indol-1-yl)phenyl]pyridine-3-carboxamide;
N- {4-[2-Methylthio-4-(2-tetrahydrofuranyl)indol-1-yl)phenyl]pyridine-3-carboxamide;
N- {4-[2-Methylthio-5-(2-tetrahydrofuranyl)indol-1-yl)phenyl]pyridine-3-carboxamide;
N- {4-[2-Methylthio-4-(3-tetrahydrofuranyl)indol-1-yl)phenyl]pyridine-3-carboxamide;
N- {4-[2-Methylthio-5-(3-tetrahydrofuranyl)indol-1-yl)phenyl]pyridine-3-carboxamide;
N- {4-[2-Methyl-4-(2-furanyl)indol-1-yl)phenyl]pyridine-3-carboxamide;
N- {4-[2-Methyl-5-(2-furanyl)indol-1-yl)phenyl]pyridine-3-carboxamide;
N- {4-[2-Methyl-4-(3-furanyl)indol-1-yl)phenyl]pyridine-3-carboxamide;
N- {4-[2-Methyl-5-(3-furanyl)indol-1-yl)phenyl]pyridine-3-carboxamide;
N- {4-[2-Cyano-4-(2-furanyl)indol-1-yl)phenyl]pyridine-3-carboxamide;
N- {4-[2-Cyano-5-(2-furanyl)indol-1-yl)phenyl]pyridine-3-carboxamide;
N- {4-[2-Cyano-4-(3-furanyl)indol-1-yl)phenyl]pyridine-3-carboxamide;
N- {4-[2-Cyano-5-(3-furanyl)indol-1-yl)phenyl]pyridine-3-carboxamide;
N- {4-[2-Methylthio-4-(2-furanyl)indol-1-yl)phenyl]pyridine-3-carboxamide;
N- {4-[2-Methylthio-5-(2-furanyl)indol-1-yl)phenyl]pyridine-3-carboxamide;
N- {4-[2-Methylthio-4-(3-furanyl)indol-1-yl)phenyl]pyridine-3-carboxamide;
N- {4-[2-Methylthio-5-(3-furanyl)indol-1-yl)phenyl]pyridine-3-carboxamide;
N- {4-[2-Methyl-4-(2-thiazolyl)indol-1-yl)phenyl]pyridine-3-carboxamide;
N- {4-[2-Methyl-5-(2-thiazolyl)indol-1-yl)phenyl]pyridine-3-carboxamide;
N- {4-[2-Cyano-4-(2-thiazolyl)indol-1-yl)phenyl]pyridine-3-carboxamide;
N- {4-[2-Cyano-5-(2-thiazolyl)indol-1-yl)phenyl]pyridine-3-carboxamide;
N- {4-[2-Methylthio-4-(2-thiazolyl)indol-1-yl)phenyl]pyridine-3-carboxamide; and
N- {4-[2-Methylthio-5-(2-thiazolyl)indol-1-yl)phenyl]pyridine-3-carboxamide.

6. A pharmaceutical composition comprising an effective amount of the compound according to claim 1 and a pharmaceutically acceptable carrier or adjuvant.

7. A pharmaceutical composition comprising an effective amount of the compound according to claim 2 and a pharmaceutically acceptable carrier or adjuvant.

8. A pharmaceutical composition comprising an effective amount of the compound according to claim 3 and a pharmaceutically acceptable carrier or adjuvant.

9. A pharmaceutical composition comprising an effective amount of the compound according to claim 4 and a pharmaceutically acceptable carrier or adjuvant.

10. A pharmaceutical composition comprising an effective amount of the compound according to claim 5 and a pharmaceutically acceptable carrier or adjuvant.

11. A method of treating an inflammatory disease which comprises administering to a patient in need of such treatment a therapeutically effective amount of a compound according to claim 1.

12. A method of treating an inflammatory disease which comprises administering to a patient in need of such treatment a therapeutically effective amount of a compound according to claim 2.

13. A method of treating an inflammatory disease which comprises administering to a patient in need of such treatment a therapeutically effective amount of a compound according to claim 3.

14. A method of treating an inflammatory disease which comprises administering to a patient in need of such treatment a therapeutically effective amount of a compound according to claim 4.

15. A method of treating an inflammatory disease which comprises administering to a patient in need of such treatment a therapeutically effective amount of a compound according to claim 5.

* * * * *